United States Patent
Burgio et al.

(10) Patent No.: US 6,875,016 B2
(45) Date of Patent: Apr. 5, 2005

(54) DENTAL IMPRESSION TRAY WITH IMPRESSION MATERIAL RETAINER

(75) Inventors: Paul A. Burgio, Grant, MN (US); Ingo W. Wagner, Woerthsee (DE)

(73) Assignees: 3M ESPE, AG, Seefeld (DE); 3M Innovative Properties Company, St. Paul, MN (US)

(*) Notice: Subject to any disclaimer, the term of this patent is extended or adjusted under 35 U.S.C. 154(b) by 210 days.

(21) Appl. No.: 10/295,540

(22) Filed: Nov. 15, 2002

(65) Prior Publication Data

US 2003/0180680 A1 Sep. 25, 2003

Related U.S. Application Data

(63) Continuation-in-part of application No. 10/105,199, filed on Mar. 25, 2002, now abandoned.

(51) Int. Cl.⁷ .................................. A61C 9/00
(52) U.S. Cl. ........................................ 433/37
(58) Field of Search ................ 433/37–48; 24/306, 24/442–452

(56) References Cited

U.S. PATENT DOCUMENTS

| | | | |
|---|---|---|---|
| 2,598,927 A | | 6/1952 | May |
| 2,963,786 A | | 12/1960 | Browning |
| 4,041,549 A | * | 8/1977 | Atkinson .................... 2/94 |
| 4,472,140 A | | 9/1984 | Lustig |
| 4,530,662 A | * | 7/1985 | Andersson et al. ........... 433/37 |
| 4,907,966 A | | 3/1990 | Kesling |
| 5,032,122 A | * | 7/1991 | Noel et al. .................. 604/391 |
| 5,316,474 A | | 5/1994 | Robertson |
| 5,379,491 A | * | 1/1995 | Solo .............................. 24/3.3 |
| 5,415,544 A | * | 5/1995 | Oxman et al. ................ 433/48 |
| 5,611,791 A | * | 3/1997 | Gorman et al. ............. 604/391 |
| 5,636,985 A | | 6/1997 | Simmen et al. |
| 5,890,895 A | | 4/1999 | Tucker |
| 5,984,911 A | * | 11/1999 | Siebers et al. .............. 604/391 |
| 6,045,359 A | | 4/2000 | Tucker |
| 6,202,264 B1 | * | 3/2001 | Ishihara ....................... 24/445 |
| 6,302,690 B1 | | 10/2001 | Brandhorst et al. |
| 6,642,160 B1 | * | 11/2003 | Takahashi .................... 442/336 |

FOREIGN PATENT DOCUMENTS

| | | |
|---|---|---|
| DE | 100 04 415 A1 | 8/2000 |
| EP | 0 096 020 A1 | 12/1983 |
| EP | 1 029 514 A1 | 8/2000 |
| FR | 2 561 908 | 10/1985 |
| WO | WO00/27302 | 5/2000 |

* cited by examiner

Primary Examiner—John J Wilson

(57) ABSTRACT

A dental impression tray comprises a trough for receiving dental impression material and at least one retainer on at least a portion of an inner surface of the trough. The retainer comprises a plurality of anchoring elements, each of which comprises a first end, a second end, and an arc between the first and second ends. The first and second ends of the anchoring elements are connected to the inner surface of the trough, and the arcs project from the inner surface of the trough. The loop material of a hook and loop mechanical fastener is a particularly useful retainer.

55 Claims, 7 Drawing Sheets

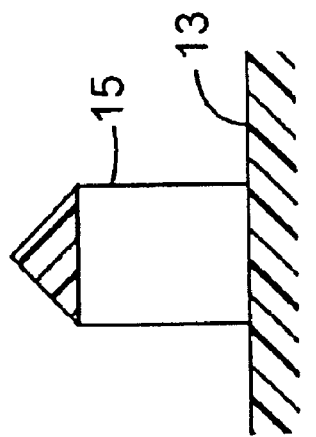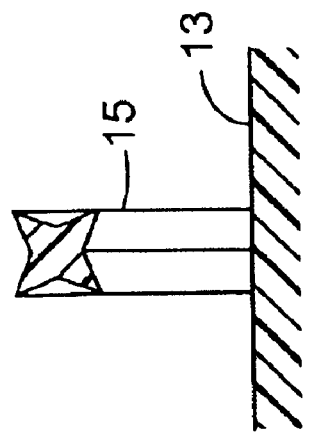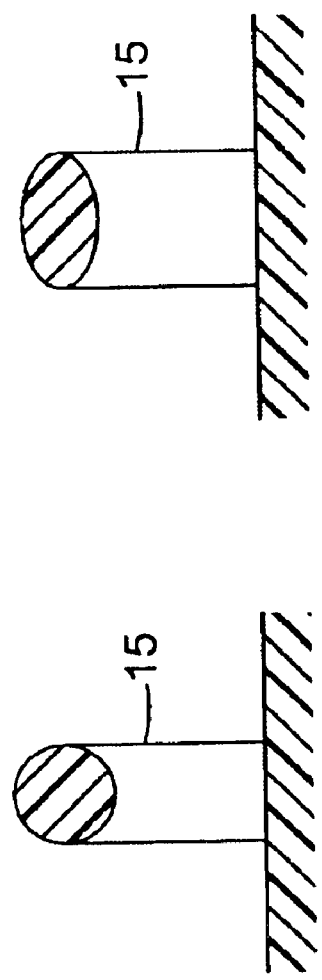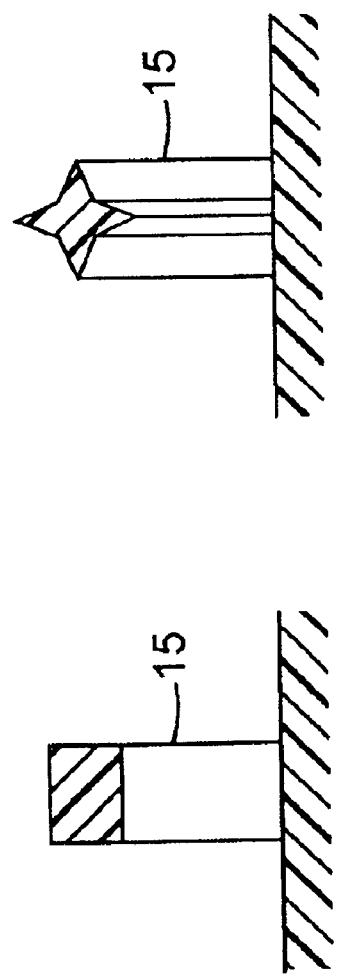

DENTAL IMPRESSION TRAY WITH IMPRESSION MATERIAL RETAINER

This patent application is a continuation-in-part of U.S. patent application Ser. No. 10/105,199, filed on Mar. 25, 2002, now abandoned which application is hereby incorporated by reference in its entirety.

BACKGROUND OF THE INVENTION

1. Technical Field

The present invention relates generally to dental impression trays and, more specifically, to dental impression trays having a dental impression material retainer incorporated therein.

2. Description of the Related Art

EP 0 096 020 B1 discloses a dental impression tray comprising a trough for receiving dental impression material and a porous felt anchoring mat. The trough is provided on at least certain portions of its inside surface with the felt mat. The felt mat serves to hold the hardened impression material in the impression tray when the impression tray is removed from the jaw. The felt mat is made up of filaments which are distributed uniformly in all directions and which lie close to each other on the inside of the trough and are attached to the latter. The filaments are fixed to each other at their contact points so that a relatively stable three-dimensional network is formed.

To use this known impression tray a flowable impression material is first introduced into the trough and then the tray is placed on the patient's jaw and pressed against the teeth. In this way, the impression material is pressed with relatively great force against the felt mat on the inside of the trough, with the result that it penetrates into the outer layer of the felt mat and the filaments of the latter become embedded in the impression material.

One disadvantage of this known impression tray is that an impression material having a relatively high viscosity may penetrate only slightly into the felt mat. For this reason, only a few filaments located on the top of the felt mat may become embedded in the impression material and, as a consequence, may be easily torn out of the hardened impression material when the impression tray is removed from the jaw, because of the high tensile forces that occur during this procedure.

The impression material may push down and compress even a thick felt mat so there will be only a limited penetration of the impression material around the filaments of a thick mat. There is a risk of the impression material detaching from the impression tray and losing its original shape, as a result of which the subsequent dental work loses out on accuracy of fit.

It is further well known in the prior art to achieve a very good "retention capacity" (i.e., a measure of the bond strength between a dental impression material and a dental impression tray) by using a dental adhesive, for example a polyvinyl siloxane adhesive available from 3M ESPE AG, Germany, with a simple dental impression tray. The adhesive is first applied with a small brush to the inner surface of the trough. Then it must dry, typical drying times being between 3 and 6 minutes, and finally the impression material is introduced into the trough. This approach may provide a better retention capacity than the known dental impression tray described in EP 0 096 020 B1, but it requires the dental professional to perform the additional steps of applying an adhesive and waiting for the adhesive to dry.

SUMMARY OF THE INVENTION

The dental impression trays of the present invention provide both good retention capacity, and quick and easy handling for the dental professional.

The dental impression trays of the present invention further provide impressions of good quality and precision.

Dental impression trays according to the invention comprise:

a trough for receiving dental impression material; and at least one retainer on at least one part of an inner surface of the trough, wherein each retainer comprises a plurality of anchoring elements, each of which comprises a first end, a second end, and an arc between the first and second ends, wherein the first and second ends of the anchoring elements are connected to the inner surface of the trough, and the arcs project from the inner surface of the trough.

The term "arc" as used in the context of the present invention means that portion of an anchoring element that projects from the inner surface of the dental impression tray trough, irrespective of the shape of the arc. Since the arcs of the anchoring elements project from the inner surface of the trough, the dental impression material flows through, between and around the arcs when the dental impression material is introduced into the impression tray. Preferably, the arcs become embedded completely in the dental impression material as the impression material hardens. Good retention capacity is achieved as a result of this.

The shape, the size and the material of the anchoring elements can easily be varied to fit different requirements and to adapt to particular circumstances. For example larger arcs can be used for higher viscosity impression materials than are used for lower viscosity impression materials.

Further preferred features and embodiments of the invention are described in the claims.

It is possible for the profile or cross section of the anchoring elements to be round, triangular, quadrangular and star-shaped. However, other profiles are also possible.

In addition, it is possible for the profile or cross section of the anchoring elements to be elongate.

In addition, the side elevation shape of the anchoring elements can be round, triangular or quadrangular. Other shapes are also possible.

Furthermore, each anchoring element can be formed by a fiber which is connected at two sections, preferably at its two ends, to the inner surface of the trough. The term "fiber" as used in the context of the present invention signifies elongate structures in the most general sense. Preferably the fibers have a stiffness which is such that the fibers do not collapse in on themselves and do not lie more or less flat on the inner surface of the trough. Desirably the fibers provide arcs that project from the inner surface of the trough.

In this case, it is possible for the fiber to form a closed arc. The term "closed arc" as used in the context of the present invention signifies a fiber whose two ends are connected to one another.

Moreover, it is possible for a plurality of anchoring elements to be formed by one fiber which has at least three sections connected to the inner surface of the trough. Consequently, such a fiber, which is connected at three sections to the inner surface of the trough, forms two anchoring elements. In general such a fiber which is connected at n sections to the inner surface of the trough, forms n-1 anchoring elements.

In this case, it is possible for the fiber to form a coil or a wave.

It is additionally possible for the anchoring elements to be arranged at uniform distances next to one another and/or behind one another.

It is also possible for the distance between anchoring elements situated next to one another to be between about 0.01 and 0.3 mm, more preferably between about 0.1 and 0.2 mm. This distance is preferably greater, the higher the viscosity of the impression material used.

In addition, it is possible for the distance between adjacent anchoring elements situated behind one another to be between about 0.01 and 3 mm, preferably between about 0.1 and 1 mm, and more preferably between about 0.4 and 0.6 mm.

Furthermore, it is possible for the length of the arc in an anchoring element to be between about 0.01 and 10 mm, preferably between about 1 and 4 mm, and more preferably between about 2 and 3 mm. This length is preferably greater, the higher the viscosity of the impression material used.

Moreover, it is possible, for each anchoring element, for the ratio between its height H and the distance A separating its ends to be between about $H/A=1$ and $H/A=0.2$, preferably between about $H/A=0.8$ and $H/A=0.4$, and more preferably between about $H/A=0.7$ and $H/A=0.5$. This ratio $H/A$ is a measure of the rough contour of the anchoring element, which consequently is preferably as high as it is wide or flat, that is lower than wider.

In addition, it is possible for the anchoring elements to be connected to the inner surface of the trough by adhesive bonding and/or fusing. Fusing includes for example sonic welding, heat fusion and extrusion bonding. However, other types of connection are also possible.

In addition, it is possible for the anchoring elements to be arranged on a base layer or intermediate layer that is connected to the inner surface of the trough. One particularly preferred example of this embodiment is a retainer that comprises loop side material for a hook and loop mechanical fastener in which a plurality of preferably polymeric loops are secured to a preferably thermoplastic base layer or intermediate layer by bonding (e.g., with an adhesive) and/or fusing (e.g., sonic welding, heat fusion or extrusion bonding). However, other types of connection are also possible. In addition to being a polymeric film, the base layer may be a planar textile material, preferably a non-woven material. In this event the anchoring elements are connected to the textile base layer by means of the fact that they extend with their connecting sections within the base layer. This may be produced, for example, by sewing.

In addition, it is possible for the base layer to be connected to the inner surface of the trough by fusing and/or adhesive bonding. Fusing includes, for example, sonic welding, heat fusion and extrusion bonding. In the case of adhesive bonding, it is possible for the base layer to be bonded to the inner surface of the trough with an adhesive layer or a double-sided adhesive tape.

In addition, it is possible for the anchoring elements and/or the base layer and/or the trough to be made of a thermoplastic material. If two of these structural parts are made of a thermoplastic material, then they can be connected by fusing, preferably sonic welding, heat fusion or extrusion bonding. If the trough is made of a thermoplastic material and has a lower melt point than the anchoring elements, the anchoring elements can be pressed into the still soft material of the trough, or the latter can be cast around them during the production of the trough, which can be done, for example, by injection-molding, pressure die-casting or thermo-forming. This applies similarly in the case where the base layer is made of a thermoplastic material and has a lower melt point than the anchoring elements, and also in the case where the trough is made of a thermoplastic material and has a lower melt point than the base layer.

In addition, it is possible for the anchoring elements to have glass and/or carbon fibers. Such anchoring elements are particularly resistant to tearing.

In addition, there are preferably substantially no interconnections between the arcs of adjacent anchoring elements so that the retainers do not comprise a three-dimensional network.

In another aspect, the invention relates to a dental impression tray comprising:

a trough for receiving dental impression material; and at least one dental impression material retainer on at least a portion of an inner surface of the trough;

wherein the dental impression tray displays a maximum tensile force of at least 30 N, more preferably a maximum tensile force of at least 40 N, when evaluated in a Retention Capacity Test without using a dental adhesive to bond the impression material to the retainer.

In still another aspect, the invention relates to a dental impression tray comprising:

a trough for receiving dental impression material; and at least one retainer arranged on at least a portion of an inner surface of the trough wherein the retainer comprises loop material of a hook and loop mechanical fastener.

In yet another aspect, the invention comprises a method of retaining a hardened dental impression material in a trough of a dental impression tray. The method comprises the steps of:

providing a dental impression tray having a trough for receiving dental impression material, and at least one retainer on at least a portion of an inner surface of the trough, wherein the retainer comprises loop material of a hook and loop mechanical fastener;

introducing a dental impression material into the trough of the dental impression tray; and allowing the dental impression material to harden, whereby the retainer retains the hardened dental impression material in the tray during use of the tray.

In another aspect, the invention relates to a dental impression tray comprising:

a trough for receiving dental impression material;

at least one retainer on at least a portion of an inner surface of the trough; and at least one strand on at least a portion of a surface of the retainer.

The one or more strands serve as a stop to the teeth if the dentist inadvertently pushes the tray against the incisal edge of the teeth. This is advantageous, because contact of the teeth with the floor of the tray can introduce defects in the impression.

It is possible that each retainer comprises a plurality of anchoring elements, each of which comprises a first end, a second end, and an arc between the first and second ends, wherein the first and second ends of the anchoring elements are connected to the inner surface of the trough, and the arcs project from the inner surface of the trough.

It is possible that the dental impression tray displays a maximum tensile force of at least 30 N when evaluated in a Retention Capacity Test without using a dental adhesive to bond the impression material to the retainer.

It is possible that the retainer comprises loop material of a hook and loop mechanical fastener.

It is possible that the retainer comprises a non-woven material.

Especially if the retainer is of one of the types mentioned above, i.e. if it comprises a plurality of anchoring elements or loop material of a hook and loop mechanical fastener or a non-woven material, then the impression material does not always go to the bottom of the pile or backing of the retainer as the impression material is filled into the tray and applied to the retainer surface. Therefore, there is an air space between the backing and the impression material. This air space creates a defect in the impression and stone model in some cases. When the dentist or patient applies too much pressure to the tray during the impression taking, the incisal edges of the teeth contact the inner surface of the tray. A defect is created whether the tooth contacts the loop material or the inner surface of the tray. A second possibility is that the impression material does infiltrate to the bottom of the retainer. The teeth can then compress the anchoring elements or the loops of the loop material or the filaments of the non-woven material, respectively, during the impression taking, but spring back when the impression is removed from the patient's mouth. This situation also causes a defect in the impression and thus the stone model.

However, the presence of the one or more strands connected to a surface of the retainer according to this invention provides a significant improvement in the quality because it reduces or eliminates loss of precision due to such detrimental defects.

In addition, it is possible that the strand prevents a tooth from contacting the retainer during use of the tray.

It is possible that the strand is arranged on a top surface of the retainer.

It is possible that the strand is continuous or discontinuous.

It is possible that the strand is straight or curved or zigzagged or bent or angled.

It is possible that a cross section of the strand is circular or oval.

It is possible that a cross section of the strand is flattened on the top surface.

It is possible that the strand is connected to a surface of the retainer.

In this case, it is possible that the strand is connected to a surface of the retainer by adhesive bonding or by fusing.

It is possible that the retainer comprises a base layer that is connected to the inner surface of the trough, and wherein the strand is arranged on and connected to the base layer.

In this case, it is possible that the strand is connected to the base layer by adhesive bonding or by fusing.

It is possible the retainer is formed of a thermoplastic material and/or the strand is formed of a thermoplastic material.

In this case, it is possible that the strand is connected to the retainer by fusing.

Moreover, the strand can be extruded onto the retainer.

BRIEF DESCRIPTION OF THE DRAWINGS

Preferred embodiments of the invention are described in more detail below with reference to the attached drawings, which are by way of example only.

FIGS. 4a to 4f are cross sections of anchoring elements with different profiles;

DETAILED DESCRIPTION OF THE PREFERRED EMBODIMENTS

Figure 1:
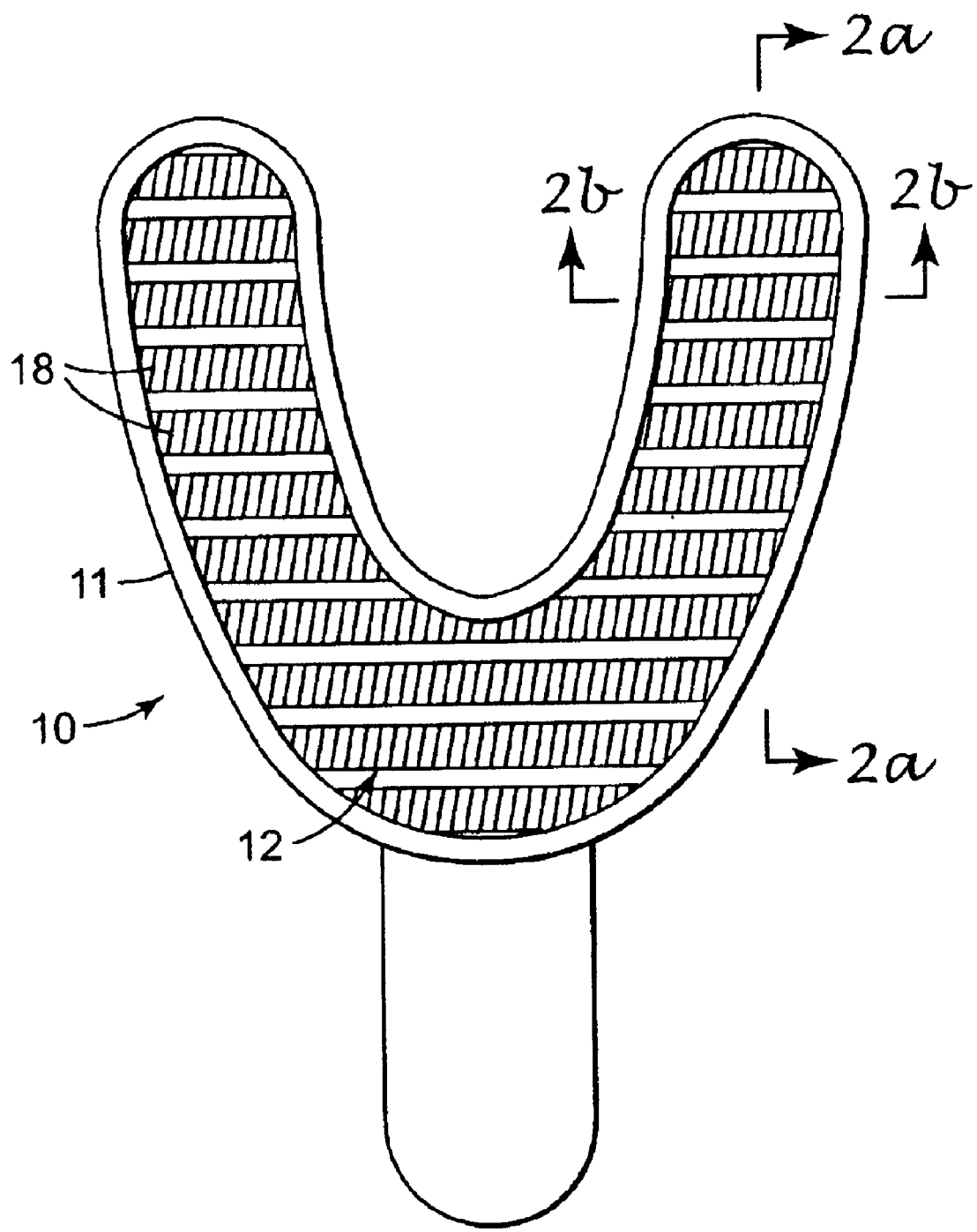
FIG. 1 is a plan view of a dental impression tray with a retainer in a first embodiment.
Figure 2A:
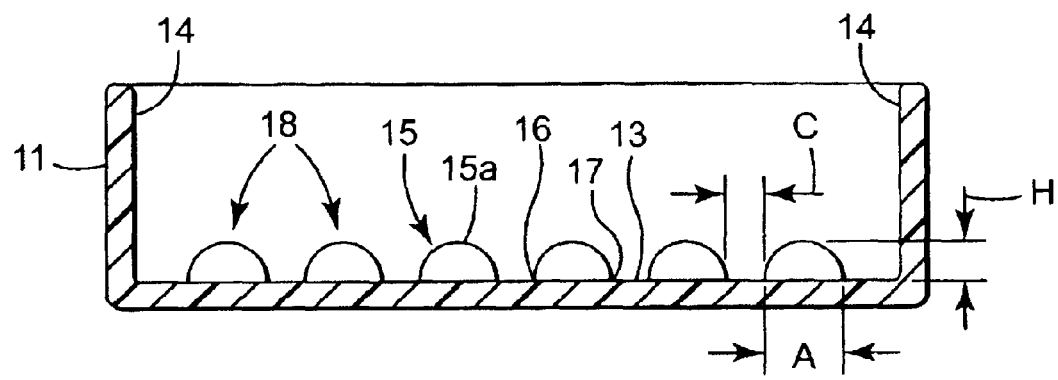
FIGS. 2a and 2b are cross sections along the lines IIa—IIa and IIb—IIb, respectively, in FIG. 1.
Figure 2B:
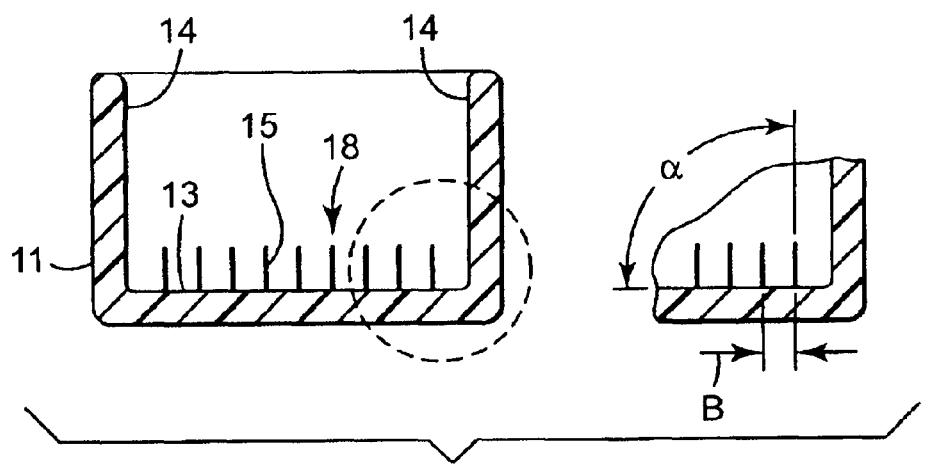

FIGS. 1 to 2b are schematic representations of a dental impression tray 10, which has a trough 11 for receiving a dental impression material (not shown) and a retainer 12 for the impression material. The retainer 12 is arranged on a base or floor 13 of the trough 11 and covers the base completely. However, retainer 12 can also be arranged on at least one partial area of the base 13 and/or on at least one partial area of side surfaces 14 of the trough 11. Collectively, base 13 and side surfaces 14 comprise the inner surface of trough 11.

The retainer 12 is shown in FIGS. 2a and 2b in a first embodiment in which it comprises a plurality of anchoring elements 15, each of which comprises an arc 15a that is connected at its two ends 16, 17 to the base 13 and projects from the latter. The anchoring elements 15 may be connected directly to the base 13, for example by adhesive bonding or fusing.

According to FIG. 1, the anchoring elements 15 are preferably arranged in a plurality of parallel rows 18 and spaced transversely from one another at uniform distances B (cf. FIG. 2b), and the rows 18 being preferably spaced longitudinally at uniform distances C (cf. FIG. 2a). However, other arrangements in which the distances B and C are not uniform or in which the rows are not parallel are also possible.

The anchoring elements 15 can project from the inner surface of the trough 11 at any desired angle α (cf. FIG. 2b), wherein α is preferably $\geq 5°$, preferably $\geq 10°$, preferably $\geq 20°$, preferably $\geq 30°$, preferably $\geq 40°$, preferably $\geq 50°$, preferably $\geq 60°$, preferably $\geq 70°$, and more preferably $\geq 80°$. Preferably, there are substantially no points of interconnection between the arcs 15a of anchoring elements 15 so that the anchoring elements of the retainer do not form a three-dimensional network. Arcs of adjacent anchoring elements are most preferably not connected.

Figure 3A:
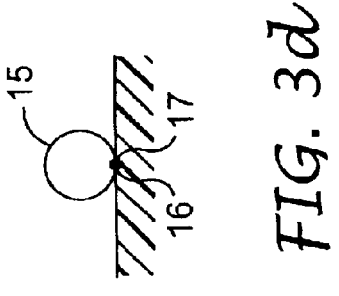
FIGS. 3a to 3h are side views of anchoring elements with different shapes.
Figure 3B:
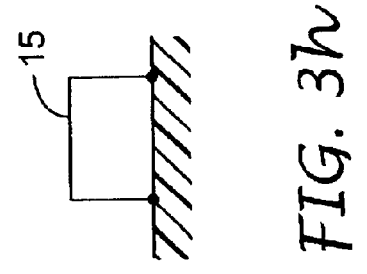
Figure 3C:
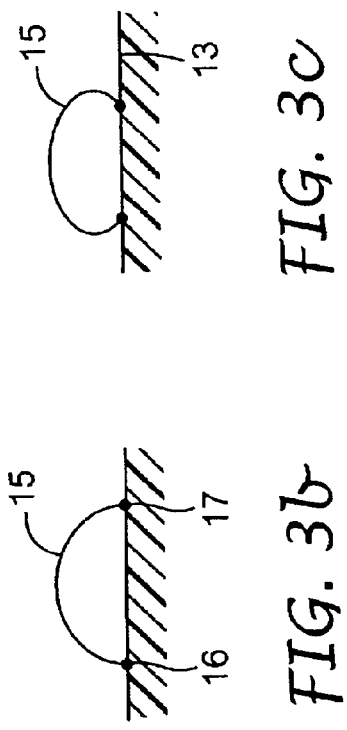
Figure 3D:
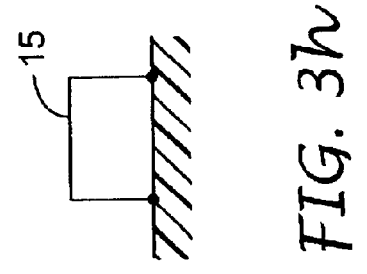
Figure 3E:
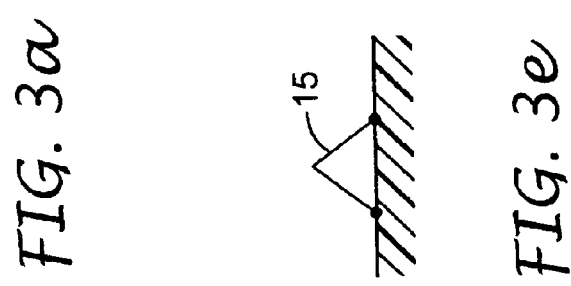
Figure 3F:
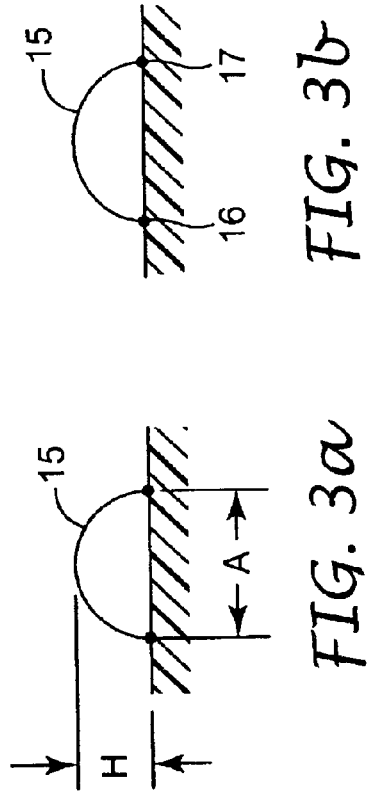
Figure 3G:
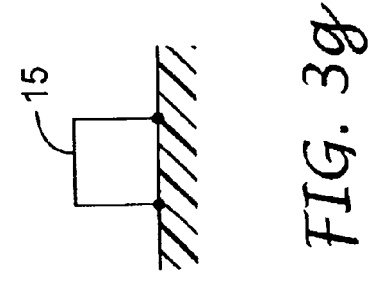
Figure 3H:
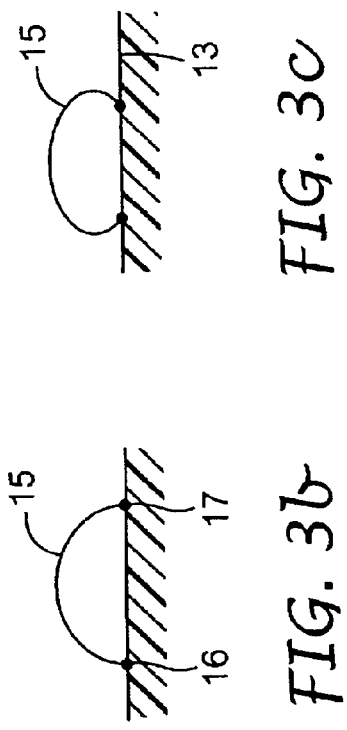

FIGS. 3a to 3h show different variants of the side elevation shape of the anchoring elements 15. However, these representations are not exhaustive and many other side elevation shapes are also possible. More specifically, FIGS. 3a to 3d each show an anchoring element 15 whose shape is round: the shape in FIG. 3a is a semicircle; the shape in FIG. 3b is a half ellipse; the shape in FIG. 3c is a three-quarter ellipse; and the shape in FIG. 3d is a circle. FIGS. 3e and 3f each show an anchoring element 15 whose shape is triangular: the shape in FIG. 3e is an equilateral triangle; and the shape in FIG. 3f is an isosceles, obtuse-angled triangle. FIGS. 3g and 3h each show an anchoring element 15 whose shape is quadrangular: the shape in FIG. 3g is a square; and the shape in FIG. 3h is a rectangle.

In each of the anchoring elements 15 in FIGS. 3a to 3c and 3e to 3h, the anchoring element's first end 16 lies at a distance A from its second end 17, whereas in the anchoring element 15 in FIG. 3d the two ends 16 and 17 are connected to the base 13 at the same point (i.e., A=O), so that this anchoring element forms a closed arc.

In each of the anchoring elements 15 in FIGS. 3a to 3c and 3e to 3h, height H, (i.e., the distance from the summit of the arc 15a to the base 13) is at most as great as the distance A between its ends 16, 17. Preferably, the ratio between the height H and the distance A (i.e., H/A) is $\leq$ about 1; however, the following approximate ratios are also useful: $0.2 \leq H/A$, preferably $0.4 \leq H/A \leq 0.8$, and more preferably $0.5 \leq H/A \leq 0.7$. Height H may be greater than distance A so that H/A is >1, provided that the corresponding anchoring element still projects from the inner surface of the trough.

FIGS. 4a to 4f show different variants for the cross-sectional profile of the anchoring elements 15. However, these representations are not exhaustive and other cross-sectional profiles are also possible. In the anchoring elements 15 in FIGS. 4a and 4b, the profile is round, more specifically a circle in FIG. 4a and an ellipse in FIG. 4b. In FIG. 4c the profile is triangular, in FIG. 4d it is quadrangular, and in FIGS. 4e and 4f it is star-shaped. The profiles in FIGS. 4b and 4d are elongate parallel to the base 13 and therefore afford particularly great resistance to a tensile force directed at right angles to the base 13.

Each anchoring element 15 can be formed by at least one fiber 19, as can be seen clearly in FIGS. 5 to 11. Each fiber may provide one, or more than one, anchoring element.

Figure 5:
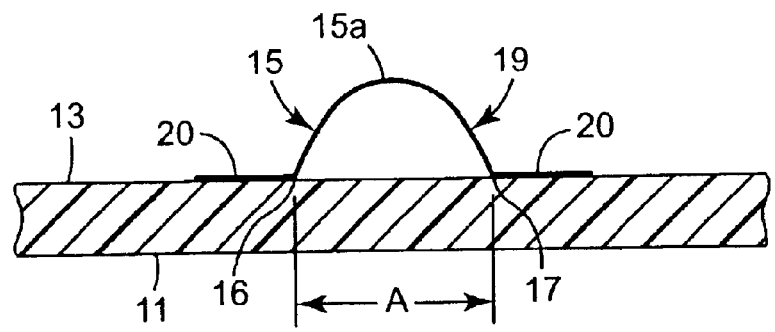
FIG. 5 is a side view of a fiber in a first embodiment.

More specifically, FIG. 5 shows a fiber 19 in a first embodiment in which it is connected to the base 13 at two connection sections, which in this case are the two end sections 20 of fiber 19, spaced at a distance A from one another. Since the arc length of the fiber section situated between the two end sections 20 is greater than the distance A, this forms an arc 15a which projects from the base 13 and represents an anchoring element 15 whose ends 16, 17 lie at this exact distance A from one another.

Figure 6:
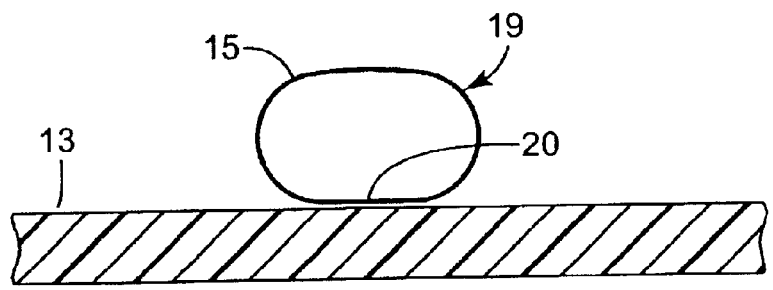
FIG. 6 is a side view of a fiber in a second embodiment.

FIG. 6 shows a fiber 19 in a second embodiment which differs from the first embodiment in FIG. 5 in that the two end sections 20 are connected to the base 13 at the same point, i.e. at the distance A=0. This fiber 19 thus forms an anchoring element 15 in the form of a closed arc.

Figure 7:
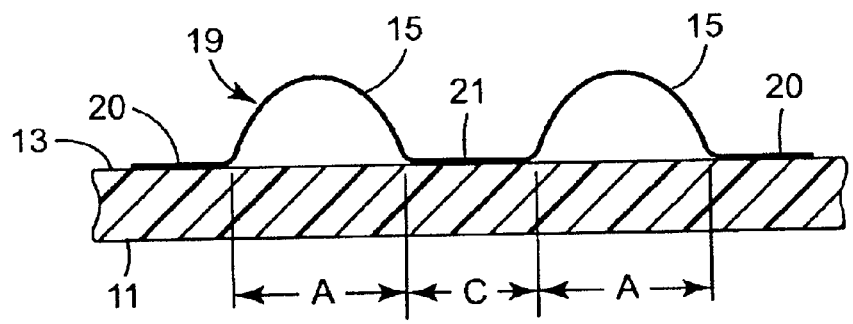
FIG. 7 is a side view of a fiber in a third embodiment.

FIG. 7 shows a fiber 19 in a third embodiment which differs from the first embodiment in FIG. 5 and from the second embodiment in FIG. 6 in that it is connected to the base 13 at three connection sections which in this case are its two end sections 20 and a middle section 21, each end section 20 being at the distance A from the middle section 21. In this embodiment, a single fiber 19 forms two anchoring elements 15 arranged one behind the other and whose distance C from one another is defined by the length of the middle section 21. The fiber 19 may be of any practical length and/or connected to the base 13 by more than three connection sections. In preferred structures, the approximate distance C between two adjacent anchoring elements 15 (situated one behind the other) is $0.01 \text{ mm} \leq C \leq 3$ mm, more preferably $0.1 \text{ mm} \leq C \leq 1$ mm, and most preferably $0.4 \text{ mm} \leq C \leq 0.6$ mm.

Figure 8:
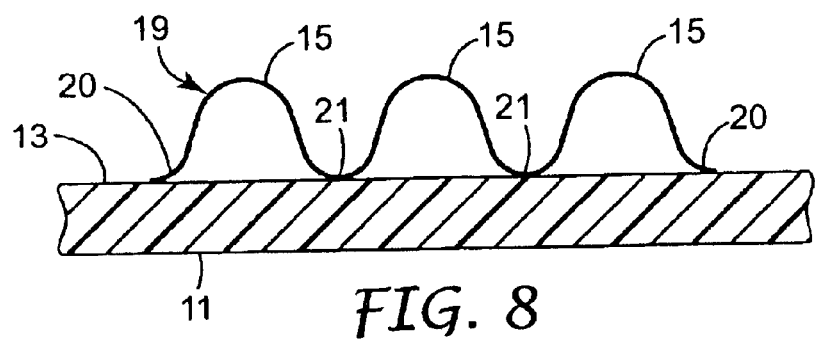
FIG. 8 is a side view of a fiber in a fourth embodiment.

FIG. 8 shows a fiber 19 in a fourth embodiment, which differs from the third embodiment in FIG. 7 in that it forms a wave.

Figure 9:
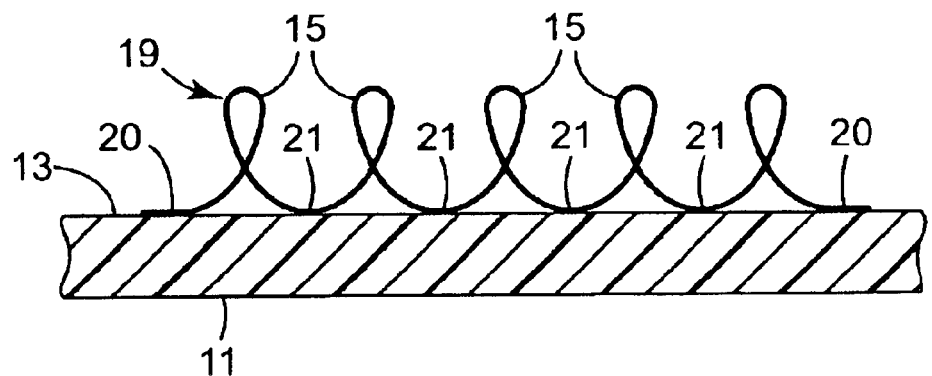
FIG. 9 is a side view of a fiber in a fifth embodiment.

FIG. 9 shows a fiber 19 in a fifth embodiment, which differs from the third embodiment in FIG. 7 and from the fourth embodiment in FIG. 8 in that it forms a coil. Fiber 19 can also assume other shapes, for example, a zigzag.

Figure 10:
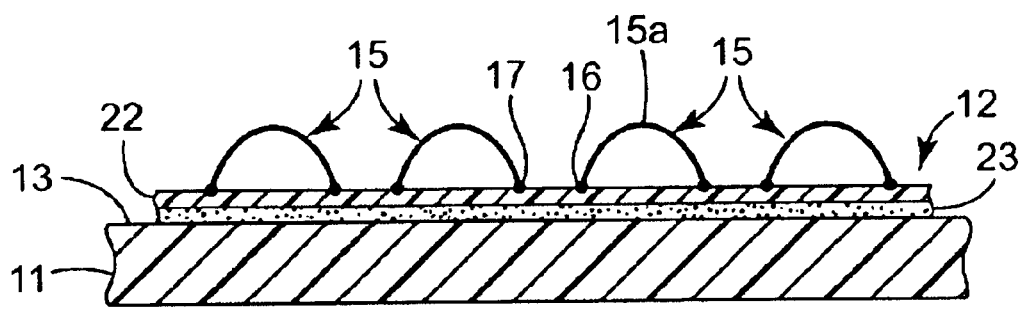
FIG. 10 is a cutaway side view of a retainer in a second embodiment.

FIG. 10 shows the retainer 12 in a second embodiment which differs from the first embodiment in FIGS. 2a and 2b in that an intermediate layer or base layer 22 is provided between the anchoring elements 15 and the inner surface of the trough 11. Here, the anchoring elements 15 are connected at their ends 16, 17 to the base layer 22 and project from the base layer. The base layer 22 is in turn connected to the trough 11. Here, both the connection between the anchoring elements 15 and the base layer 22, and the connection between the base layer 22 and the trough 11, can be made by adhesive bonding or fusing. However, other types of connection are also possible. The embodiment shown in FIG. 10 may be regarded as one in which the anchoring elements project from the inner surface of the trough 11, because the base or intermediate layer 22 is connected to the trough's inner surface. As explained more fully below, embodiments that employ a base or intermediate layer offer certain advantages.

The base layer 22 is shown in FIG. 10 in a first embodiment in which it is a continuous sheet. The continuous sheet may be adhesively bonded to the trough 11 using, for example, an adhesive layer 23 or a double-sided adhesive tape (not shown). The retainer 12 of FIG. 10 is preferably constructed from a sheet of loop material that is laminated to an adhesive layer 23, cut to the proper shape, and then adhered to the trough of an otherwise conventional dental tray. One type of loop material that can be used in this construction is of the type used to form the loop side of a hook and loop mechanical fastener. (Hook and loop mechanical fasteners employ a loop material that mates with or mechanically engages a hook material to form a single use fastener or a fastener that can be opened and closed multiple times.) Briefly, loop materials useful in the invention include a backing (typically comprising a thermoplastic film having generally uniform morphology) with a multiplicity of loops formed thereon or otherwise attached thereto. The loops are generally arranged as longitudinally oriented, generally non-deformed fibers.

Referring again to FIG. 10, the backing of the loop material provides intermediate or base layer 22, and the fibers of the loop material provide anchoring elements 15. The anchoring elements can be bonded, fused or otherwise attached to the base layer 22 (i.e., the backing) at spaced locations so as to provide the ends 16, 17 of the anchoring elements, and the arcs 15a that project from the inner surface of the trough.

Loop material useful in the invention can be made by forming a sheet of longitudinally oriented polymeric fibers in which the fibers have arcs that project in the same direction between spaced connection sections, and then forming at least a portion of the backing around the spaced connection sections, for example by extruding thermoplastic material onto the connection sections so that the arcs of the fibers project from a front or top surface of the newly formed backing. The individual fibers may be formed from many polymeric materials such as polypropylene, polyethylene, polyester, nylon or polyamide, or combinations of such materials (e.g., a core of polyester and a sheath of polypropylene) and may comprise polymers of or one or more materials.

A sheet of loop material that is smooth on one side and looped in a regular pattern on the other side may be laminated to an adhesive layer by conventional processing techniques. For example, a sheet of loop material may be laminated to the exposed adhesive layer on a polyester film that is coated on both sides with a high-tack pressure sensitive adhesive, and having a silicone-coated release liner protecting the other adhesive layer. With conventional rotary die processing equipment, the resulting laminated sheet of loop materials may be cut (without cutting through the release liner) into U-shaped retainers of a size that fits onto at least a portion of the inner surface of the trough of a conventional dental impression tray. The resulting U-shaped retainers having an adhesive surface may remain on the release liner to be wound and stored in roll form for later processing, for example by a converting machine that removes the U-shaped retainers from the release liner, and places and adheres the retainers onto the inner surface of troughs of conventional injected-molded plastic dental trays.

Figure 11:
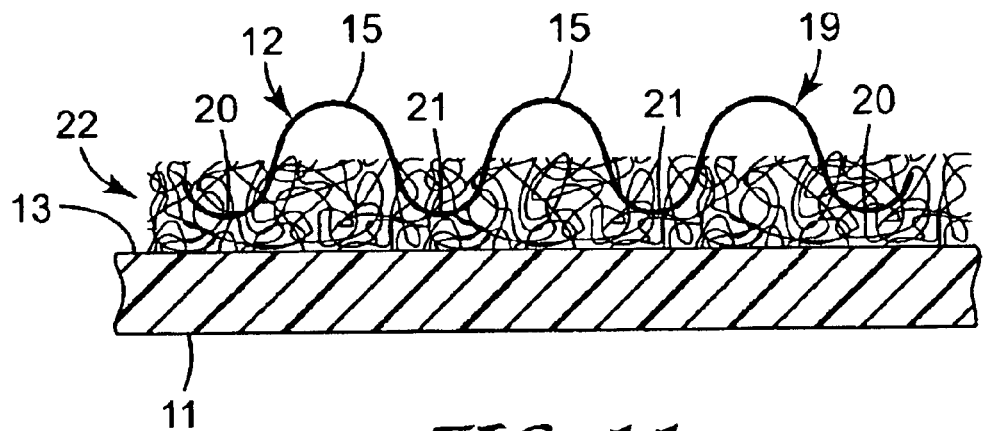
FIG. 11 is a cutaway side view of a retainer in a third embodiment.

FIG. 11 shows a base layer 22 in a second embodiment in which the base layer is a non-woven material. However, it can also be another planar textile structure, for example a woven fabric or a knitted fabric. In FIG. 11, the fibers 19 are connected to the base layer 22 by means of the fact that they extend with their connection sections 20, 21 within the base layer. This course is therefore like a stitch, and it can be produced, for example, by means of the fibers 19 being surrounded by the textile fibers during production of the planar textile structure comprising the base layer 22, or by means of the fibers 19 being sewn into the finished planar textile structure.

Figure 12:
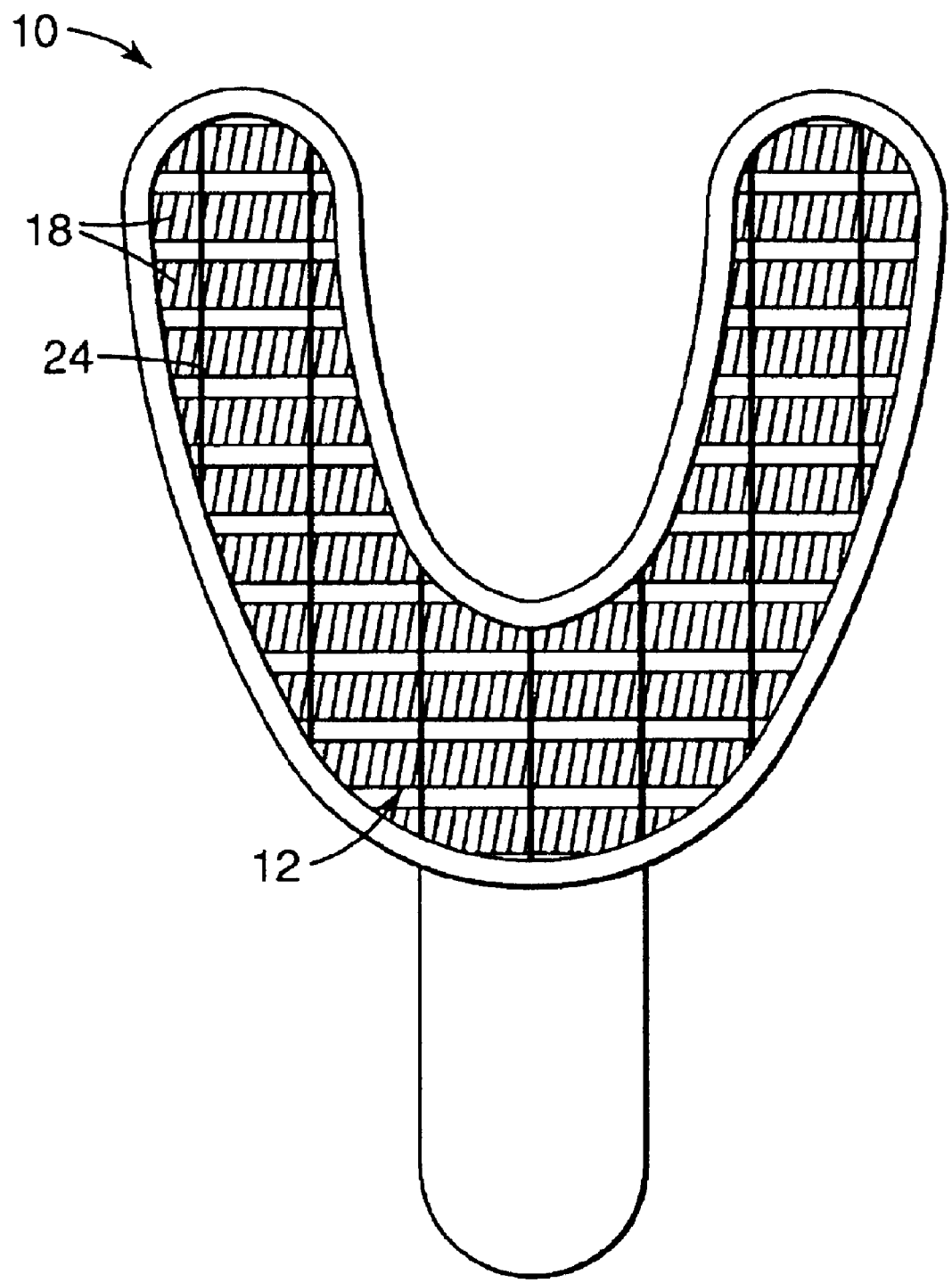
FIG. 12 is a plan view of a dental impression tray of FIG. 1 further comprising strands on the retainer.

FIG. 12 shows a dental impression tray 10 that is similar to that shown in FIG. 1, but further comprises seven strands 24. These strands 24 are arranged on and connected to the retainer 12. They are straight and oriented essentially perpendicular to the rows 18 of anchoring elements 15. The strands 24 may be connected directly to the retainer 12, for example by adhesive bonding or by fusing, or may be connected to a base layer 22, as is described for the anchoring elements 15 of FIG. 10. Alternatively, the strands 24 may be connected directly to both the retainer 12 and the base layer 22.

The strands 24 can be variously spaced from every ⅜th inch (9.5 mm) across the width of the tray 10, or there can be two or more strands 24 in the center of the tray 10 that would contact the anterior teeth. The strands 24 can be continuous and straight as in FIG. 12. However they can also be discontinuous or interrupted or curved or zigzagged or bent or angled. A cross section of the strands 24 can be circular or oval or flattened on the top surface. The strands 24 can be oriented anterior to posterior or left to right or at some angle in between these points.

In the following, a manufacturing process for placing strands on loop material of a hook and loop mechanical fastener is described by way of example.

The strands may be formed from polypropylene using a strand extruder. The extruder heats the polypropylene and forces the molten material through a series of holes in the head of the extruder. The size of the holes and the pressure and temperature settings of the extruder determine the size of the strand. The strand is formed as the molten polymer exits the hole in the head and then contacts and fuses to the loop material that is moved by a conveyer beneath the extruded strand. For example, a head that has holes ⅜ inch (9.5 mm) apart creates strands that are ⅜ inch (9.5 mm) apart on the loop material. The material with the molten strands can then go through a chilled nip roller to control the height of the strands and thus make a more uniform height across the width of the material. The material containing the cooled strands is then wound on a roll. This wound material is then run through a conventional rotary converting process to laminate an adhesive layer and cut out the retainer insert that is placed in the impression tray.

Instead of the polypropylene, any other suitable thermoplastic material can be used to form the strands. Moreover, instead of the loop material, any other suitable retainer material, such as for example a non-woven material or the felt anchoring mat of EP 0 096 020 B1, can be used as well.

Such strands extruded onto surface of retainer material, enhance the function of this material in an impression tray.

EXAMPLE

Retention Capacity Test

In this example the retention capacity of a dental impression tray according to the invention was evaluated by measuring in a first test cycle the tensile strength (tensile force) of the bond formed between an impression material and a known dental adhesive typically used to bond an impression material to a simple tray, by measuring in a second test cycle the tensile strength of the bond formed between the same impression material and a dental tray according to the invention, and by then comparing the results of the two test cycles. The tensile strength of the bond formed between the dental impression material and the retainer is a measure of the retention capacity of a dental tray according to the invention as determined according to the Retention Capacity Test described herein.

More specifically, a universal tensile test machine "UPM 1435" from ZWICK out-fitted with a 5 kN force sensor, and a pair of 27 mm diameter brass test plates was prepared for the first test cycle by the following steps:

Cleaning the facing surfaces of the test plates with alcohol.

Applying a thin, uniform layer of a polyvinyl siloxane dental adhesive available from 3M ESPE AG, Germany, to each of the two facing surfaces of the cleaned test plates.

Allowing the adhesive to dry for 5 minutes.

Preparing 5 g of "POSITION PENTA QUICK" impression material available from 3M ESPE AG, Germany, by using a "PENTAMIX 2" impression material mixing and delivery system available from 3M ESPE AG, Germany, according to the manufacturer instructions.

Applying the prepared impression material to the lower test plate and placing the upper test plate in a parallel position and on top of the applied impression material.

Pressing the two test plates together until the impression material forms a uniform layer of 2 mm in thickness.

Curing the impression material for 10 minutes and removing the excess impression material that was squeezed out between the two test plates.

The retention capacity was then measured by the following steps:

Attaching the prepared upper and lower test plates vertically to the upper and lower jaws of the universal tensile test machine, moving the upper and lower jaws away from each other at a rate of 1 mm/minute, and recording the maximum tensile force that was detected. This test procedure was performed a total of six times, and the results were averaged.

For the second test cycle, the test equipment was prepared according to the following steps:

Cleaning the facing surfaces of the test plates with alcohol, as in the first test cycle.

Applying to each of the two facing surfaces of the test plates a 27 mm diameter retainer according to the invention and formed from loop material having a general construction similar to the embodiment shown in FIG. 10 (3M product no. KN 1971, available from 3M Company, USA).

The further steps, namely preparing, applying and curing 5 g of "POSITION PENTA QUICK" impression material between two pressed together test plates was the same as in the first test cycle. This test procedure was performed a total of four times, and the results were averaged.

The first test cycle yielded an average maximum tensile force (a measure of retention capacity) of 65 N (standard deviation=8.7). The second test cycle yielded an average maximum tensile force of 41.3 N (standard deviation=2.53).

Preferably a dental impression tray displays a retention capacity (average maximum tensile force between the impression material and the tray) of at least 35 N, more preferably at least 40 N. Thus, a dental tray according to the invention has good retention capacity and compares favorably to the retention capacity of a conventional impression tray that uses a dental adhesive to bond the impression material to the tray.

In addition, the dental impression tray of the invention is both quick and easy for the dental professional to use. Preferably the tray comes prefabricated with the retainer(s) already attached to the inner surface of the trough. It is further possible to deliver the tray and one or more retainers in a kit, wherein the retainers may be of different kinds adapted for particular uses, as for example with impression materials of different viscosity. Then the dental professional will apply the appropriate retainer(s) to the desired portion(s) of the inner surface of the dental tray trough before filling the tray with impression material. This is especially easy if the retainers are precut to fit to the dental tray and are supplied on a removable liner that covers the adhesive surface on the bottom of the retainers.

The present invention has now been described with reference to several embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

What is claimed is:

1. A dental impression tray comprising:
a trough for receiving dental impression material;
at least one retainer on at least a portion of an inner surface of the trough; and
at least one strand on at least a portion of a surface of the retainer, wherein each retainer comprises a plurality of anchoring elements, each of which comprises a first end, a second end, and an arc between the first and second ends, wherein the first and second ends of the anchoring elements are connected to the inner surface of the trough, and the arcs project from the inner surface of the trough.

2. The impression tray as claimed in claim 1, wherein the side elevation shape of the anchoring elements is round, triangular or quadrangular.

3. The impression tray as claimed in claim 1, wherein a cross section of the anchoring elements is round, triangular, quadrangular or star-shaped.

4. The impression tray as claimed in claim 1, wherein the cross section of the anchoring elements is elongate.

5. The impression tray as claimed in claim 1, wherein each anchoring element is formed by a fiber that is connected at two sections to the inner surface of the trough.

6. The impression tray as claimed in claim 5, wherein the fiber forms a closed arc.

7. The impression tray as claimed in claim 1, wherein the plurality of anchoring elements is formed by a fiber that contains at least three sections that are connected to the inner surface of the trough.

8. The impression tray as claimed in claim 7, wherein the fiber forms a coil.

9. The impression tray as claimed in claim 7, wherein the fiber forms a wave.

10. The impression tray as claimed in claim 1, wherein the anchoring elements are arranged at uniform distances next to one another and/or behind one another.

11. The impression tray as claimed in claim 10, wherein the uniform distance between anchoring elements next to each other is about 0.01 to 0.3 mm.

12. The impression tray as claimed in claim 10, wherein the uniform distance between anchoring elements situated behind each other is about 0.01 to 3 mm.

13. The impression tray as claimed in claim 1, wherein the length of the arc of each anchoring element is about 0.01 to 10 mm.

14. The impression tray as claimed in claim 1, wherein for each anchoring element the ratio of its height H and a distance A separating its first and second ends is about 1 to 0.2.

15. The impression tray as claimed in claim 1, wherein the anchoring elements are connected to the inner surface of the trough by adhesive bonding.

16. The impression tray as claimed in claim 1, wherein the anchoring elements are connected to the inner surface of the trough by fusing.

17. The impression tray as claimed in claim 1, wherein the anchoring elements are arranged on a base layer that is connected to the inner surface of the trough.

18. The impression tray as claimed in claim 17, wherein the anchoring elements are connected to the base layer by adhesive bonding.

19. The impression tray as claimed in claim 17, wherein the anchoring elements are connected to the base layer by fusing.

20. The impression tray as claimed in claim 17, wherein the base layer is a continuous sheet.

21. The impression tray as claimed in claim 17, wherein the base layer is a planar textile.

22. The impression tray as claimed in claim 21, wherein the anchoring elements are connected to the base layer by connecting sections that extend into the planar textile base layer.

23. The impression tray as claimed in claim 17, wherein the base layer is connected to the inner surface of the trough by adhesive bonding.

24. The impression tray as claimed in claim 23, wherein the base layer is bonded to the inner surface of the trough with a double-sided adhesive tape.

25. The impression tray as claimed in claim 17, wherein the base layer is connected to the inner surface of the trough by fusing.

26. The impression tray as claimed in claim 1, wherein the anchoring elements comprise a thermoplastic material.

27. The impression tray as claimed in claim 1, wherein the anchoring elements contain glass and/or carbon fibers.

28. The impression tray as claimed in claim 1, wherein there are substantially no interconnections between the arcs of adjacent anchoring elements.

29. A dental impression tray comprising:
a trough for receiving dental impression material;

at least one dental impression material retainer on at least a portion of an inner surface of the trough; and at least one strand on at least a portion of a surface of the retainer;

wherein the retainer comprises loop material of a hook and loop mechanical fastener; and wherein the dental impression tray displays a maximum tensile force of at least 30 N when evaluated in a Retention Capacity Test without using a dental adhesive to bond the impression material to the retainer.

30. The impression tray as claimed in claim 29, wherein the dental impression tray displays a maximum tensile force of at least 40 N, when evaluated in a Retention Capacity Test without using a dental adhesive to bond the impression material to the retainer.

31. A dental impression tray comprising:

a trough for receiving dental impression material;

at least one retainer on at least a portion of an inner surface of the trough; and at least one strand on at least a portion of a surface of the retainer, wherein the retainer comprises loop material of a hook and loop mechanical fastener, and wherein each retainer comprises a plurality of anchoring elements, each of which comprises a first end, a second end, and an arc between the first and second ends, wherein the first and second ends of the anchoring elements are connected to the inner surface of the trough, and the arcs project from the inner surface of the trough.

32. The impression tray as claimed in claim 31, wherein the loop material comprises a polymeric backing having a multiplicity of loops formed thereon or otherwise attached thereto.

33. The impression tray as claimed in claim 32, wherein the retainer is adhesively bonded to the inner surface of the trough.

34. The impression tray as claimed in claim 33, wherein the loops are formed of a polymeric material and are fused to the backing.

35. A method of retaining a hardened dental impression material in a trough of a dental impression tray, the method comprising the steps of:

providing a dental impression tray having a trough for receiving dental impression material, at least one retainer on at least a portion of an inner surface of the trough, and at least one strand on at least a portion of a surface of the retainer, wherein the retainer comprises loop material of a hook and loop mechanical fastener;

introducing a dental impression material into the trough of the dental impression tray; and allowing the dental impression material to harden, whereby the retainer retains the hardened dental impression material in the tray during use of the tray.

36. The method of claim 35 wherein the dental impression tray displays a maximum tensile force of at least 30 N when evaluated in a Retention Capacity Test without using a dental adhesive to bond the impression material to the retainer.

37. The method of claim 35 wherein the dental impression tray displays a maximum tensile force of at least 40 N when evaluated in a Retention Capacity Test without using a dental adhesive to bond the impression material to the retainer.

38. A dental impression tray comprising:

a trough for receiving dental impression material;

at least one retainer on at least a portion of an inner surface of the trough; and at least one strand on at least a portion of a surface of the retainer, wherein the retainer comprises loop material of a hook and loop mechanical fastener.

39. The impression tray as claimed in claim 38, wherein the dental impression tray displays a maximum tensile force of at least 30 N when evaluated in a Retention Capacity Test without using a dental adhesive to bond the impression material to the retainer.

40. The impression tray as claimed in claim 38, wherein the retainer comprises a non-woven material.

41. The impression tray as claimed in claim 38, wherein the strand prevents a tooth from contacting the retainer during use of the tray.

42. The impression tray as claimed in claim 38, wherein the strand is arranged on a top surface of the retainer.

43. The impression tray as claimed in claim 38, wherein the strand is continuous or discontinuous.

44. The impression tray as claimed in claim 38, wherein the strand is straight or curved or zigzagged or bent or angled.

45. The impression tray as claimed in claim 38, wherein a cross section of the strand is circular or oval.

46. The impression tray as claimed in claim 38, wherein a cross section of the strand is flattened on the top surface.

47. The impression tray as claimed in claim 38, wherein the strand is connected to a surface of the retainer.

48. The impression tray as claimed in claim 47, wherein the strand is connected to the surface of the retainer by adhesive bonding.

49. The impression tray as claimed in claim 47, wherein the strand is connected to the surface of the retainer by fusing.

50. The impression tray as claimed in claim 47, wherein the retainer comprises a base layer that is connected to the inner surface of the trough, and wherein the strand is arranged on and connected to the base layer.

51. The impression tray as claimed in claim 50, wherein the strand is connected to the base layer by adhesive bonding.

52. The impression tray as claimed in claim 50, wherein the strand is connected to the base layer by fusing.

53. The impression tray as claimed in claim 50, wherein the retainer is formed of a thermoplastic material and/or the strand is formed of a thermoplastic material.

54. The impression tray as claimed in claim 53, wherein the strand is connected to the retainer by fusing.

55. The impression tray as claimed in claim 53, wherein the strand is extruded onto the retainer.

* * * * *